United States Patent
Suzuki et al.

[11] 3,944,628
[45] Mar. 16, 1976

[54] METHOD FOR THE SEPARATION OF HYDROCARBONS

[75] Inventors: Yoshiaki Suzuki, Machida; Hajime Mori; Takemi Nakanome, both of Yokohama, all of Japan

[73] Assignee: Mitsubishi Chemical Industries, Ltd., Tokyo, Japan

[22] Filed: Apr. 4, 1973

[21] Appl. No.: 347,764

[30] Foreign Application Priority Data
Apr. 7, 1972  Japan .................... 47-35015
June 8, 1972  Japan .................... 47-57097
June 15, 1972  Japan .................... 47-59727
June 27, 1972  Japan .................... 47-64304
July 13, 1972  Japan .................... 47-70252
Aug. 2, 1972  Japan .................... 47-77399

[52] U.S. Cl. .......... 260/674 N; 260/430; 260/666 A; 260/674 R; 260/677 A; 260/681.5 C
[51] Int. Cl.² .......................................... C07C 7/01
[58] Field of Search ........ 260/666 A, 677 A, 674 K, 260/674 A, 674 N, 674 W, 674 C, 674 SE, 681.5 C, 430, 674 N

[56] References Cited
UNITED STATES PATENTS

| | | |
|---|---|---|
| 2,768,986 | 10/1956 | Johnson et al. .................... 260/674 |
| 2,798,891 | 7/1957 | Schaeffer .......................... 260/674 |
| 3,401,112 | 9/1968 | Dunlop et al. ..................... 260/674 |
| 3,634,530 | 1/1972 | Bills ................................ 260/674 |
| 3,763,200 | 10/1973 | Dines ............................... 260/430 |

*Primary Examiner*—Delbert E. Gantz
*Assistant Examiner*—C. E. Spresser
*Attorney, Agent, or Firm*—Sughrue, Rothwell, Mion, Zinn & Macpeak

[57] ABSTRACT

Hydrocarbons are reacted with a silver tri-halogenomethane sulfonate of the formula

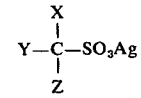

wherein X, Y and Z each represents a halogen atom, to form the corresponding complexes, and then the thus formed complexes are decomposed to selectively separate the desired hydrocarbon components. The used silver tri-halogenomethane sulfonate also is recovered by the decomposition of the complexes.

2 Claims, No Drawings

METHOD FOR THE SEPARATION OF HYDROCARBONS

BACKGROUND OF THE INVENTION

1. FIELD OF THE INVENTION

This invention relates to a method for separating hydrocarbons, and more precisely, a method for separating specifically determined hydrocarbons from other hydrocarbons as well as for separating the specified hydrocarbons into the respective structural isomers.

2. DESCRIPTION OF THE PRIOR ART

Aromatic hydrocarbons such as xylene, styrene, etc., olefins and some other kinds of condensed polycyclic hydrocarbons are extremely important in the field of petroleum industries in these days as raw materials of synthetic resins, synthetic rubbers and other high molecular compounds and as raw materials of various kinds of derivatives, and these hydrocarbons substances are obtained from feed materials such as petroleum products, cracked gasolines, tar products, etc. for example by means of distillation or the like. For example, xylene is separated in general from petroleum reformates, etc. as mixed xylene by means of various kinds of distillation operation, and the thus obtained mixed xylene is further separated into the respective isomers by means of various methods and the thus separated isomers are collected. As the method for separating the mixed xylene into the respective isomers, various kinds of methods have been known, for example, fractional distillation, solvent extraction, adsorption chromatography, low-temperature processing, etc. However, all these methods require very complicated operations.

Olefinic hydrocarbons of four or more carbon atoms have various kinds of isomers, and these hydrocarbons are separated into the respective isomers by means of precision fractional distillation, extraction, extractive distillation, adsorption chromatography by Molecular Sieves, etc. Condensed polycyclic hydrocarbons are separated from tar products, petroleum products, etc. as raw materials by means of precision fractional distillation, extraction, crystallization, etc. after a light oil fraction has been distilled and separated. However, these methods require fairly complicated steps and the operation thereof also is fairly troublesome.

The inventors have studied the separation of hydrocarbons and in the result have found that a silver tri-halogenomethane sulfonate may form complexes with certain kinds of hydrocarbons, that the complex forming ability of the sulfonate varies, depending upon the kinds of hydrocarbons, and that the formed complexes may easily be decomposed by means of water to recover the hydrocarbons and the silver tri-halogenomethane sulfonate. On these grounds, the inventors have attained a new technical art to separate and purify various kinds of hydrocarbons by using the formation of complexes with the silver tri-halogenomethane sulfonate.

SUMMARY OF THE INVENTION

The object of the present invention is to provide a new method for separating and purifying hydrocarbons.

Another object of the present invention is to provide a method for separating hydrocarbons by forming complexes of hydrocarbons and a silver tri-halogenomethane sulfonate and then decomposing the formed complexes.

Still another object of the present invention is to provide a method for separating hydrocarbons into the respective structural isomers.

DETAILED DESCRIPTION OF THE INVENTION

The silver tri-halogenomethane sulfonate which may form complexes with hydrocarbons and which is used in the present invention is represented by the following formula:

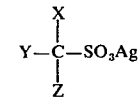

wherein X, Y and Z each represents a halogen atom. The silver tri-halogenomethane sulfonate may easily be prepared, for example, from a tri-halogenomethane sulfonic acid and silver oxide.

The halogen atom represented by X, Y and Z in the formula includes fluorine, chlorine, bromine and iodine atoms, and in particular, fluorine and chlorine atoms are preferred. The halogen atoms of these X, Y and Z may be identical or different. For example, silver tri-fluoromethane sulfonate, silver difluoromonochloromethane sulfonate, silver mono-fluoro-dichloromethane sulfonate, silver trichloromethane sulfonate, etc. are mentioned. These silver salts often separate silver deposits in the presence of light or radiation ray, and so it is desirable to treat the same in a dark place.

The complex forming reaction between the silver trihalogenomethane sulfonate and hydrocarbons varies, depending upon the kinds of the hydrocarbons. For example, the reaction of the silver salt with ortho-xylene, meta-xylene and styrene is an equimolecular reaction, while the silver salt reacts with para-xylene and ethyl-benzene in the molar ratio of 2:1 and with a di-alkyl-naphthalene in the molar ratio of 2:1 or 4:1.

Accordingly, the amount of the silver tri-halogenomethane sulfonate to be used varies, depending upon the kinds of the respective hydrocarbons to be separated in the form of complexes, and at least the stoichiometric amount in the reaction of forming complexes with the hydrocarbons to be separated is required. The stoichiometric amount of the silver salt required for the formation of complexes with the respective hydrocarbons is previously experimentally determined. If it is not required to separate the whole amount of the desired hydrocarbons contained in the raw material mixture, the silver salt is used in a smaller amount than the stoichiometric amount thereof, and if the desired hydrocarbons are to be obtained in a highly pure form, the amount of the silver salt to be used is preferably smaller than the stoichiometric amount thereof.

In general, the silver salt is used in an amount of 0.5 –2.0 times as much as the stoichiometric amount thereof required for the formation of complexes with hydrocarbons to be separated.

The hydrocarbons to form complexes with the silver tri-halogenomethane sulfonate are aromatic hydrocarbons substituted by hydrocarbyl groups, unsaturated aliphatic hydrocarbons, unsaturated cycloaliphatic hydrocarbons and condensed polycyclic hydrocarbons.

The aromatic hydrocarbons substituted by hydrocarbyl groups are aromatic hydrocarbons having on the benzene nucleus thereof one or more alkyl, vinyl, cycloalkyl, aryl and aralkyl groups, and these groups may have a linear chain or branched chain, and the aryl group and the vinyl group may have further substituents. Representatives of these aromatic hydrocarbons are, for example, toluene; $C_8$-$C_{10}$ aromatic hydrocarbons as shown in the following Table 1; $C_{11}$ alkyl benzenes such as diisopropylbenzene; styrene; styrene derivatives such as $\alpha$-methyl-styrene, $\beta$-methyl-styrene, o-, m-, p-vinyl-toluene, cis-, trans-stilbene, etc. In addition, cycloalkyl benzenes such as cyclohexyl-benzene and aryl substituted benzenes such as diphenyl derivatives, e.g., diphenyl, terphenyls, methyl-diphenyls, ethyl-diphenyls, isopropyldiphenyls, etc. may also be used in the present invention.

Table 1 ortho-xylene, para-xylene, meta-xylene,
isopropyl-benzene, 1-methyl-3-n-propylbenzene,
n-propylbenzene, n-butylbenzene,
1-methyl-3-ethylbenzene, 1-methyl-4-n-propylbenzene
1-methyl-4-ethylbenzene, 1,2-diethylbenzene,
1,3,5-trimethylbenzene, 1,4-diethylbenzene,
1-methyl-2-ethylbenzene, 1,3-dimethyl-5-ethylbenzene,
t-butylbenzene, 1-methyl-2-n-propylbenzene,
1,2,4-trimethylbenzene, 1,4-dimethyl-2-ethylbenzene,
isobutylbenzene, 1,3-dimethyl-4-ethylbenzene,
s-butylbenzene, 1,2-dimethyl-4-ethylbenzene,
1-methyl-3-isopropylbenzene,1,3-dimethyl-2-ethylbenzene,
1,2,3-trimethylbenzene, 1,2-dimethyl-3-ethylbenzene,
1-methyl-4-isopropylbenzene, 1,2,4,5-tetramethylbenzene,
1-methyl-2-isopropylbenzene, 1,2,3,5-tetramethylbenzene,
1,3-diethylbenzene, 1,2,3,4-tetramethylbenezene, The unsaturated aliphatic hydrocarbons and the unsaturated cycloaliphatic hydrocarbons are olefinic hydrocarbons represented by the following formula:

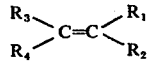

wherein $R_1$, $R_2$, $R_3$ and $R_4$ each represents hydrogen or an alkyl cycloalkyl, alkenyl or cycloalkenyl group, and $R_2$ and $R_4$ may form an alkylene or alkenylene group and $R_1$ and $R_2$ may form an alkenylene group.

Representatives of these hydrocarbons are, for example, linear or branched mono-olefins such as ethylene, propylene, butene, iso-butene, heptene, hexene, pentene, 2-methyl-2-pentene, octene, etc.; polyolefins such as 1,3-butadiene, isoprene, 1,4-pentadiene, 1,2-pentadiene, 1,3-hexadiene, 1,5-hexadiene, octadiene, hexatriene, octatriene, etc.; cyclic olefins such as cyclopropene, cyclobutene, cyclopentene, cyclohexene, cycloheptene, cyclobutadiene, cyclopentadiene, cyclohexadiene, cyclooctatriene, etc.; alkyl substituted cyclic olefins such as methyl-cyclopropene, methylcyclobutene, ethyl-cyclobutene, methyl-cyclohexene, etc. In addition, cycloalkyl substituted olefins such as vinyl-cyclohexane, vinylcyclohexene, etc. as well as methylene-cyclopropane, methylene-cyclohexane, etc. may also be mentioned.

The condensed polycyclic hydrocarbons contain 4 or more carbon atoms, and are, for example, indene, naphthalene, azulene, methyl-naphthalene, ethyl-naphthalene, biphenylene, acenaphthylene, dimethyl-naphthalene, fluorene, phenalene, anthracene, phenanthrene, pyrene, chrysene, naphthacene, triphenylene, etc. as well as partially hydrogenated derivatives of these polycyclic hydrocarbons such as di-, tetra- and hexa-hydro derivatives thereof. In addition, these hydrocarbons may further be substituted by an alkyl group, cycloalkyl group, aryl group, aralkyl group, etc.

For the formation of complexes of the silver tri-halogenomethane sulfonate and these hydrocarbons, the silver tri-halgenomethane sulfonate may be contacted with liquid or gaseous hydrocarbons. In this formation, the silver salt may be solid and need not be always in the form of a solution.

For example, to a liquid hydrocarbons or a solution of paraffin or cycloparaffin containing hydrocarbons is added a solid silver tri-halogenomethane sulfonate and mixed. In this case, the mixture may be heated or cooled, if necessary. In general, however, the mixing may well be performed at normal temperature and the mixture is preferably somewhat stirred. The formed complexes are sometimes dissolved in excess hydrocarbons and sometimes are separated. Next, place, after the excess hydrocarbons have been distilled off or the mixture has been cooled or otherwise a paraffin such as hexane or cyclohexane has been added to the mixture, the solid complexes may be separated. However, it is not always necessary to separate the complexes, and after impurities contained in the mixture have been removed, the formed complexes may be successively subjected to the next decomposition treatment. In addition, the existence of water on the formation of the complexes interferes with the formation, and so it is desired that the formation of the complexes is carried out in a dry state.

Another embodiment for forming hydrocarbon-silver salt complexes is to introduce a gaseous material containing hydrocarbons into a column wherein a solid silver tri-halogenomethane sulfonate on a porous carrier such as alumina, silica, sellaite, titania, magnesia, pumice, active charcoal, etc. to which the solid silver salt has been adsorbed has been filled, to form the desired complexes. In this introduction, the gaseous material is introduced at normal pressure or under a reduced pressure or in the presence of an inert gas carrier such as dried nitrogen gas, and, if necessary, under heat. The temperature of the formation of the complexes may freely be selected in the scope ranging from low temperature to 200°C, and is preferably selected in the range of 0°–120°C. In some cases, the complex forming reaction is an exothermic reaction, and in such cases, it is necessary to cool the reaction system by appropriate means and to keep the temperature thereof constant.

The thus formed complexes may easily be decomposed by bringing the same into contact with water thereby the recover the silver tri-halogenomethane sulfonate and hydrocarbons. For example, when the complexes are put into water at normal temperature, the complexes are decomposed and the recovered silver tri-halogenomethane sulfonate is dissolved in water, and the hydrocarbons are separated as an oil layer or crystals. The thus freed hydrocarbons are separated or extracted by using a solvent such as praffin whereby the hydrocarbons are recovered and collected. The silver tri-halogenomethane sulfonate may easily be recovered and collected by distilling out the water. Or otherwise, the complexes may be decomposed by contacting the same with steam. In the latter case, the silver tri-halogenomethane sulfonate remains as a solid, and the hydrocarbons only flow out together with the steam. Accordingly, by repeatedly operating the formation of complexes where a gaseous mixture containing hydrocarbons is introduced into a column filled with a carrier to which a silver tri-halogenomethane sulfonate has been adsorbed and the decomposition of the formed complexes to follow where steam is introduced into the column, the hydrocarbons may continuously be separated.

In any cases as mentioned above, the amount of water to be used is not limited, and is, in general, applied in a molar ratio from 1 to 500 to the silver tri-halogenomethane sulfonate forming the complexes. However, if the amount of the water is too much, such is not preferable from the economical view-point in that the recovering step of the silver salt would become expensive. Accordingly, water is preferably used in a mole ratio from 1 to 100, more preferably 3 to 50.

The treating temperature on this water addition is not so high, since if the temperature is too high, decomposition of hydrocarbons themselves to be separated or coloration thereof would sometimes occur. In general, the temperature is selected in the range of 0°–200°C, preferably 0°–130°C.

As mentioned above, the complex forming ability between the silver tri-halogenomethane sulfonate and the hydrocarbons varies depending upon the structures of the reagents. Accordingly, by utilizing the difference and by appropriately selecting the conditions on the operation or by repeating the complex formation, complexes of specific hydrocarbons may selectively be formed and thus the specified hydrocarbons may be separated and collected. For example, with respect to xylene-complex forming ability between xylene and the silver tri-halogenomethane sulfonate, para-xylene has the highest ability, and ortho-xylene, meta-xylene and ethyl-benzene have gradually lower abilities in this order. Accordingly, it is possible to selectively separate the para-xylene as the xylene-complex from a mixed xylene or from a mixture of xylene and other hydrocarbons, or it also is possible to separate the para-xylene from the mixed xylene at first, and in the next place, to separate the ortho-xylene from the residue and then analogously to separate the meta-xylene and the ethyl-benzene in this order. In this separation, if the purity of the specified concentrated component in the separated xylene is not sufficiently high, the purity may easily be improved by repeatedly performing the formation of the silver tri-halogenomethane sulfonate-xylene complexes.

With respect to styrene groups, the complex forming ability between the styrene groups and the silver tri-halogenomethane sulfonate is stronger than that of other aromatic hydrocarbons, and thus the styrene groups preferentially form the complexes. Accordingly when a mixture of ethylbenzene and styrene is used, the styrene almost selectively forms a complex. In addition, the complex forming ability also varies depending upon the kinds of the isomers, and thus, it is possible to separate a mixture of cis- and trans-isomers of stilbene or a mixture of o-, m- and p-isomers of vinyl-toluene into the respective pure isomers by utilizing the difference in the complex forming ability thereof with the silver tri-halogenomethane sulfonate. Furthermore, it also is possible to separate the desired styrene from other hydrocarbons contained in the styrene mixture or to separate the desired styrene isomer from other isomers and further to increase the purity of the separated styrene by repeatedly performing the complex formation. In addition, it also is possible to successively separate 2,6-dimethyl-, 1,6-dimethyl-, 1,2-dimethyl- and 2,3-dimethyl-naphthalene isomers contained in a tar which is called a methyl-naphthalene fraction or in a mixture of petroleum products, or to mutually separate $\alpha$- and $\beta$-methylnaphthalenes from each other. Moreover it further is possible to separate naphthalene and the partial hydrogenated product thereof, tetralin, from each other, or to separate anthracene and phenathrene isomers from each other. In addition, the present invention may be adapted for other various uses, say as follows: Successive separation and collection of butadiene, 1-butene, cis- and trans-2-butenes and iso-butylene from a $C_4$ fraction which is called a BB fraction; separation and collection of dienes such as cyclobutadiene, piperylene, isoprene, etc. and various kinds of monoolefin isomers from a $C_5$ fraction; separation of 1,4-cyclohexadiene from reaction mixture thereof prepared by electrolytic reduction of benzene; mutual separation of benzene, cyclohexene, cyclohexane, etc.

The method of the present invention may be combined with the conventional separation method of condensed polycyclic hydrocarbons which has hitherto been proposed. For example, when the present invention is applied to a distilled and fractionated product, cooled and separated product, recrystallized product, etc., it is possible to increase the purities of these products. For example, it of course is possible to use petroleum reformates, cracked gasolines, isomer mixtures obtained from the alkylation of benzene or toluene, etc. as the raw materials of aromatic hydrocarbons and to directly adapt the method of the present invention for the raw materials. Apart from this, it also is possible to previously separate one or more aromatic hydrocarbons from aromatic hydrocarbon mixtures by means of the conventional distillation method, separation method, solvent extraction method or the like which has hitherto been proposed, and afterwards to separate the respective components by applying the method of the present invention. Otherwise, after one or more aromatic hydrocarbons have previously been separated by means of the method of the present invention, afterwards a conventional distillation method, separation method, solvent extraction method or the like may be combined with the former method thereby to separate the respective components. The combination of the present method and a conventional method is appropriately determined from the relative difficulty of the process and the economical viewpoint.

In addition, when hydrocarbons of high polymerizability are to be treated, it also is possible to perform the present process under the presence of a phenol series or amine series polymerization inhibitor, for the purpose of inhibiting the polymerization of the hydrocarbons used.

Now, the present invention will be explained more in detail by the following examples; which, however, do not whatsoever limit the scope of the present invention.

EXAMPLE 1

5.0 g of silver trifluoromethane sulfonate ($CF_3SO_3Ag$) and a mixture of 2.15g of para-xylene and 2.07g of meta-xylene were heated and stirred at 100°C for 1 hour. Next, the xylene was distilled out at 100°C under reduced pressure of 100 mmHg to obtain 6.1g of white powders.

To these powders was added 20 ml of water, whereby the powders were dissolved and the xylene was separated. The separated xylene was analyzed by means of gas chromatography, whereby it was confirmed that the xylene consists of 98.5% of para-xylene and 1.5% of meta-xylene.

On the other hand, when the aqueous solution was concentrated, 5.0g of silver trifluoromethane sulfonate were recovered.

EXAMPLE 2

To 32.5g of mixed xylene consisting of 12.2% of paraxylene, 43.6% of ethyl-benzene, 29.4% of meta-xylene and 14.8% of ortho-xylene were added 2.58g of silver trifluoromethane sulfonate crystals, and the whole was heated at 90°C for 10 minutes whereby the crystals were completely dissolved. Next, the formed solution was cooled at 20°C and 1.99g of precipitated crystals were separated.

The crystals were dissolved in water to free the xylene, and the freed xylene was analyzed by means of gas chromatography. The result was as follows:

| | |
|---|---|
| para-xylene | 0.31g |
| ethyl-benzene | 0.02 g |
| meta-xylene | 0.01g |
| ortho-xylene | trace |

EXAMPLE 3

To 17.5g of the same mixed xylene as in Example 2 were dispersed 10.29g of silver trifluoromethane sulfonate powders, and the whole was stirred at 20°C for 1 hour. Next, the xylene was distilled out at 40°C under reduced pressure of 10 mmHg to obtain 12.47g of crystals.

To the thus obtained crystals were added dropwise 10g of water at 90°C under reduced pressure of 80 mmHg and the system distilled, whereby the freed xylene was distilled out together with steam, and the xylene was cooled and condensed. The thus obtained xylene was analyzed by means of gas chromatography and the result as follows:

| | |
|---|---|
| para-xylene | 1.50g |
| ethyl-benzene | 0.43g |
| metha-xylene | 0.15g |
| ortho-xylene | 0.10g |

EXAMPLE 4

A glass column having a diameter of 1.0cm and a length of 25cm was filled with 6.00g of silver trifluoromethane sulfonate powders. This column was kept at 90°C, and 9.69g of gaseous mixed xylene consisting of 12.2% of para-xylene, 43.6% of ethyl-benzene, 29.4% of meta-xylene and 14.8% of ortho-xylene were passed therethrough under reduced pressure of 60 mmHg and in the course of 1.5 hours. Next, without purging the apparatus with any other gas, 10.0g of steam was passed through the column at 90°C under reduced pressure of 60 mmHg and the steam which had flowed therethrough was cooled to condense the xylene. The obtained xylene was analyzed by means of gas chromatography, and the result was as follows:

| | |
|---|---|
| para-xylene | 0.119 g |
| ethyl-benzene | 0.0885 g |
| metha-xylene | 0.059 g |
| ortho-xylene | 0.0236 g |

EXAMPLE 5

1.91g of xylene mixture consisting of 22.4% of ethyl-benzene, 23.4% of para-xylene, 25.3% of meta-xylene and 28.6% of ortho-xylene were mixed with 1.147g of silver trichloromethane sulfonate ($Cl_3CSO_3Ag$) at room temperature, and then the excess xylene was distilled out under reduced pressure of 3 mmHg whereby 1.357g of white powders were obtained.

To these powders were added 10 ml of water to dissolve the powders, and 0.21g of xylene was separated as an oily substance. The thus separated xylene was analyzed by means of gas chromatography and the result is shown hereunder. It is noted that the para-xylene was concentrated.

| | |
|---|---|
| ethyl-benzene | 4.0% |
| para-xylene | 69.3% |
| meta-xylene | 9.3% |
| ortho-xylene | 17.3% |

EXAMPLE 6

4.22g of xylene mixture consisting of 51.0% of para-xylene and 49.0% of meta-xylene were mixed with 6.130g of silver trichloromethane sulfonate at room temperature, and then the excess xylene was distilled out under reduced pressure of 3 mmHg to obtain 7.182g of white powders.

To these powders were added 20ml of water to dissolve the powders, and 1.05g of oily xylene were separated. The thus separated xylene was analyzed by means of gas chromatography, and the result was as follows:

| | |
|---|---|
| para-xylene | 90.5% |
| meta-xylene | 9.5% |

EXAMPLE 7

1.91g of xylene mixture consisting of 22.4% of ethyl-benzene, 23.4% of para-xylene, 25.3% of meta-xylene and 28.6% of ortho-xylene were mixed with 1.160g of silver difluoro-chloromethane sulfonate ($F_2ClCSO_3Ag$) at room temperature, and then the excess xylene was distilled out under reduced pressure of 3 mmHg to obtain 1.384g of white powders.

To the obtained powders were added 10 ml of water to dissolve the same, and 0.22g of oily xylene was separated. The separated xylene was analyzed by means of gas chromatography, and the result was as follows:

| | |
|---|---|
| ethyl-benzene | 3.5% |
| para-xylene | 77.6% |
| meta-xylene | 7.0% |
| ortho-xylene | 11.9% |

COMPARATIVE EXAMPLE

In the above mentioned Example 5, silver methane sulfonate ($CH_3SO_3Ag$) was used in place of the silver trichloromethane sulfonate, and the xylene mixture was treated analogously. No complex forming ability was seen with the silver methane sulfonate.

EXAMPLE 8

3.32g of mixture consisting of 50% of styrene and 50% of ethyl-benzene were mixed with 1.00g of a silver trifluoromethane sulfonate at room temperature, and then the excess styrene and ethylbenzene were distilled out under reduced pressure of 3 mmHg to obtain 1.39g of white powders. To the white powders were added 10 ml of water to dissolve the powders, and 0.39g of water-insoluble oily material was obtained. The oily material was dissolved in cyclohexane and the resulting cyclohexane solution was analyzed by means of gas chromatography. It was confirmed that the oily composition consisted of 97.9% of styrene and 2.1% of ethyl-benzene. Thus, the styrene was extremely concentrated. Apart from this, silver methane sulfonate was used in place of the silver trifluoromethane sulfonate and the same procedure as in the above was carried out, but no complex could be formed in a stable state.

EXAMPLE 9

3.32g of mixture consisting of 50% of styrene and 50% of para-xylene were mixed with 1.16g of a silver trichloromethane sulfonate at room temperature, and then the excess styrene and para-xylene were distilled out under reduced pressure of 3 mmHg to obtain 1.56g of white powders. To the thus obtained white powders were added 10 ml of water to dissolve the same, and 0.40g of oily material was separated. The oily material was dissolved in n-hexane and the resulting n-hexane solution was analyzed by means of gas chromatography, whereby it was confirmed that the oily composition consisted of 96.8% of styrene and 3.2% of paraxylene.

EXAMPLE 10

A gaseous mixture consisting of 50% of styrene and 50% of ethyl-benzene was introduced into a covered glass column which was filled with 10 ml of a pumice of 50 mesh size carrying 1.01g of silver trifluoromethane sulfonate, under a speed of 2.30 g/hr and in the course of 30 minutes, at a temperature of 100°C. Afterwards, 20g of steam were further introduced into the column for 30 minutes under reduced pressure of 500 mmHg to cool and collect the flowage. The oily material of the upper layer was extracted with n-hexane and was analyzed by means of gas chromatography. It was confirmed that the oily material consisted of 82.1% of styrene and 17.9% of ethyl-benzene. The yield was 0.41g.

EXAMPLE 11

5g of naphtha cracked oil consisting of 42.0% of styrene, 9.2% of ortho-xylene, 18.0% of meta-xylene, 8.9% of para-xylene, 9.8% of ethyl-benzene and balance 12.1% miscellaneous were mixed with 2.01g of silver trifluoromethane sulfonate at room temperature, and then excess hydrocarbons were distilled out under the reduced pressure of 3 mmHg to obtain 2.80g of white solid powders. To the powders were added 20 ml of a water to obtain 0.81g of water-insoluble oily material. This oily material contained 87.0% of styrene.

EXAMPLE 12

3.52g of composition consisting of 50% of α-methylstyrene and 50% of cumene were mixed with 1.01g of silver trifluoromethane sulfonate at room temperature, and then the excess hydrocarbons were distilled out under reduced pressure of 3 mmHg to obtain 1.41g of white solid powders. To the powders were added 10 ml of water to obtain 0.42g of water-insoluble oily material. The oily material was analyzed by means of gas chromatography and it was confirmed that the material contained 89% of α-methyl-styrene.

EXAMPLE 13

To 2.65g of a composition consisting of 29.7% of para-vinyltoluene and 70.3% of meta-vinyl-toluene were added 1.03g of silver trifluoromethane sulfonate and the system dissolved at room temperature. Afterwards, the excess hydrocarbons were distilled out under reduced pressure of 1 mmHg to obtain 1.37g of white solid powders. To the powders were added 10 ml of water to obtain 0.34g of waterinsoluble oily material. The thus obtained oily material was analyzed by means of gas chromatography and it was confirmed that the material consisted of 52.3% of para-vinyl-toluene and 47.7% of meta-vinyl-toluene.

EXAMPLE 14

1.071g of mixture consisting of 51.3% of 1-methyl-4-isopropyl-benzene (para-cymene) and 48.7% of 1-methyl-3-isopropylbenzene (meta-cymene) were mixed with 1.036% of silver trifluoromethane sulfonate and the whole was stirred for 10 minutes at 60°C. Afterwards, the excess cymene was distilled out under reduced pressure of 5 mmHg to obtain 1.295g of white powders.

To the powders were added 10 ml of water and the whole was stirred to dissolve the powders, whereby 0.25g of oily cymene was separated. The thus separated cymene was collected and analyzed by means of gas chromatography, and the result is shown hereunder. It was confirmed that para-cymene was concentrated.

| | |
|---|---|
| 1-methyl-4-isopropyl-benzene (para-cymene) | 82.3% |
| 1-methyl-3-isopropyl-benzene (metha-cymene) | 17.7% |

EXAMPLE 15

1.150g of mixture consisting of 44.4% of para-ethyltoluene, 48.6% of meta-ethyltoluene and 7.0% of ortho-ethyltoluene were mixed with 1.039g of silver trifluoromethane sulfonate, and the whole was stirred for 30 minutes at 50°C. Next, the excess ethyltoluene was distilled out under reduced pressure of 10 mmHg to obtain 1.268g of white powders.

The powders were put into 10 ml of water to obtain 0.23g of oily material.

The thus obtained oily material was analyzed by means of gas chromatography, and the result is shown hereunder. It was confirmed that para-ethyltoluene was concentrated.

| | |
|---|---|
| para-ethyltoluene | 96.1% |
| meta-ethyltoluene | 3.9% |
| ortho-ethyltoluene | — |

EXAMPLE 16

1.145g of a ethyltoluene mixture of the same composition as in Example 15 were mixed with 1.026g of silver trichloromethane sulfonate, and after the whole was stirred at 50°C for 30 minutes, the excess ethyltoluene was distilled out under reduced pressure of 10 mmHg to obtain 1.301g of white powders.

The thus obtained white powders were put into 10 ml of water to obtain 0.27g of oily material.

The thus obtained oily material was analyzed by means of gas chromatography, and the result is shown hereunder. It was confirmed that para-ethyltoluene was concentrated.

| | |
|---|---|
| para-ethyltoluene | 91.3% |
| meta-ethyltoluene | 8.5% |
| ortho-ethyltoluene | 0.2% |

EXAMPLE 17

2.92g of a mixture consisting of 31.9% of 1,2,3-trimethylbenzene (hemimellitene), 34.6% of 1,2,4-trimethylbenzene (pseudocumene) and 33.5% of 1,3,5-trimetylbenzene (mesitylene) were mixed with 1.049g of silver trifluoromethane sulfonate, and left for 1 hour at room temperature. Afterwards, the excess trimethylbenzene was distilled out under reduced pressure of 3 mmHg to obtain 1.474g of white powders.

The thus obtained white powders were put into 10 ml of water to dissolve the powders, whereby 0.425g of oily material was obtained. The thus obtained oily material was analyzed by means of gas chromatography, and the result was as follows:

| | |
|---|---|
| 1,2,3-trimethylbenzene | 53.5% |
| 1,2,4-trimethylbenzene | 43.9% |
| 1,3,5-trimethylbenzene | 2.6% |

EXAMPLE 18

2.14g of mixture consisting of 49% of 1,2,3,5-tetramethylbenzene (isodurene) and 51% of 1,2,4,5-tetramethylbenzene (durene) were mixed with 1.022g of silver trifluoromethane sulfonate at 60°C. Afterwards, the excess tetramethylbenzene was distilled out at 60°C under reduced pressure of 0.2 mmHg to obtain 1.510g of white powders.

To the thus obtained powders were added 10 ml of water and 5 ml of n-hexane, and the n-hexane layer was analyzed by means of infrared spectrophotometer, and the result was as follows:

| | |
|---|---|
| 1,2,4,5-tetra-methylbenzene | 81% |
| 1,2,3,5-tetra-methylbenzene | 19% |

EXAMPLE 19

2.01g of mixture consisting of a 37.1% of n-butylbenzene, 31.9% of sec.-butylbenzene and 31.0% of tert.-butylbenzene were mixed with 0.695g of silver trifluoromethane sulfonate at 90°C to dissolve the silver salt. Next, the excess butylbenzene was distilled out at 50°C under reduced pressure of 0.5 mmHg to obtain 0.991g of white powders. To the thus obtained powders were added 10 ml of water to obtain 0.300g of oily material. The thus obtained oily material was analyzed by means of gas chromatography and the result was as follows:

| | |
|---|---|
| n-butylbenzene | 63.4% |
| sec.-butylbenzene | 22.8% |
| tert.-butylbenzene | 13.8% |

EXAMPLE 20

0.67g of a mixture consisting of 48.5% of 1-hexene and 51.5% of 2-hexene was mixed with 0.534g of silver trifluoromethane sulfonate at room temperature to dissolve the silver salt. The excess hexene was distilled out at room temperature under reduced pressure of 10 mmHg to obtain 0.689g of white powders. To the thus obtained powders were added 10 ml of water to separate an oily material. The oily material was analyzed by means of gas chromatography, and the result was as follows:

| | |
|---|---|
| 1-hexene | 57.3% |
| 2-hexene | 42.7% |

EXAMPLE 21

1.87g of a mixture consisting of 33.4% of cyclohexene, 32.8% of 1,4-cyclohexadiene and 33.7% of benzene were mixed with 1.168g of silver trifluoromethane sulfonate at 60°C, and then the excess $C_6$ compounds were distilled out at room temperature under reduced pressure of 20 mmHg to obtain 1.646g of white powders.

To the thus obtained powders were added 10 ml of water to obtain 0.48g of oily material. The oily material was analyzed by means of gas chromatography, and the result was as follows:

| | |
|---|---|
| cyclohexene | 4.6% |
| 1,4-cyclohexadiene | 92.5% |
| benzene | 2.8% |

EXAMPLE 22

1.03g of a mixture consisting of 51.8% of 1,3-pentadiene and 48.2% of 2-methyl-1,3-butadiene were mixed with 1.288g of silver trifluoromethane sulfonate at 10°C to dissolve the silver salt. Afterwards, the excess $C_5$ compounds were distilled out at room temperature under reduced pressure of 100 mmHg to obtain 1.532g of white powders. To the thus obtained powders were added 10 ml of water and 5 ml of n-hexane and the whole was shaken. Afterwards, the n-hexane layer was analyzed by means of gas chromatography, and the result was as follows:

| | |
|---|---|
| 1,3-pentadiene | 82.9% |
| 2-methyl-1,3-butadiene | 17.1% |

EXAMPLE 23

3.38g of a mixture consisting of 29.7% of α-methylnaphthalene and 70.3% of β-methyl-naphthalene were mixed with 0.90g of silver trifluoromethane sulfonate at 90°C. Next, the resulting mixture was cooled to room temperature, and 10 ml of n-hexane were added thereto, and then the precipitated crystals were separated by filtration. The yield of the crystals was 1.15g. Afterwards, the crystals were washed further with n-hexane. Next, 10 ml of water and 10 ml of n-hexane were added to the crystals and shaken to separate the n-hexane layer. The n-hexane layer was analyzed by means of gas chromatography and the result was as follows:

| | |
|---|---|
| α-methylnaphthalane | 16.5% |
| β-methylnaphthalene | 83.5% |

EXAMPLE 24

0.92g of a mixture consisting of 27.3% of 1,6-dimethylnaphthalene, 37.2% of 2,6-dimethylnaphthalene and 35.5% of 2,3-dimethylnaphthalene was mixed with 0.241g of silver trifluoromethane sulfonate at 100°C, and the same after-treatment as in Example 23 was carried out. The yield of this crystals was 0.313g. The result on the analysis by gas chromatography is shown hereunder. It was confirmed that 2,6-dimethylnaphthalene was concentrated.

| | |
|---|---|
| 1,6-dimethylnaphthalene | 12.0% |
| 2,6-dimethylnaphthalene | 81.2% |
| 2,3-dimethylnaphthalene | 6.8% |

EXAMPLE 25

1.86g of mixture consisting of 51.6% of indane and 48.4% of indene were mixed with 1.08g of silver trifluoromethane sulfonate at 50°C, and then the same after-treatment as in Example 23 was carried out. The yield of the crystals was 1.54g. The result of analysis by gas chromatography is shown hereunder. It was confirmed that indene was concentrated.

| | |
|---|---|
| indane | 12.7% |
| indene | 87.3% |

While the invention has been described in detail and with reference to specific embodiments thereof, it will be apparent to one skilled in the art that various changes and modifications can be made therein without departing from the spirit and scope thereof.

What we claim is:

1. The method for separating methyl naphthalenes where a mixture of α-methyl naphthalene and β-methyl naphthalene is reacted with silver tri-fluoromethane sulfonate to form complexes of β-methyl naphthalene, then the formed complexes are separated from the mixture and decomposed with water to free β-methyl naphthalene.

2. The method for separating dimethyl naphthalene where a mixture of 1,6-, 2,6-, and 2,3- dimethyl naphthalene is reacted with silver tri-fluoromethane sulfonate to form complexes of 2,6-dimethyl naphthalene selectively, then the formed complexes are separated and decomposed with water to separate 2,6-dimethyl naphthalene.

* * * * *